US009861672B2

(12) United States Patent
Worthington et al.

(10) Patent No.: US 9,861,672 B2
(45) Date of Patent: Jan. 9, 2018

(54) ANTISEPTICS

(75) Inventors: Tony Worthington, Birmingham (GB); Tarja Karpanen, Birmingham (GB)

(73) Assignee: INSIGHT HEALTH LIMITED (GB)

( * ) Notice: Subject to any disclaimer, the term of this patent is extended or adjusted under 35 U.S.C. 154(b) by 1012 days.

(21) Appl. No.: 12/674,889

(22) PCT Filed: Aug. 21, 2008

(86) PCT No.: PCT/GB2008/002832
§ 371 (c)(1),
(2), (4) Date: Feb. 23, 2010

(87) PCT Pub. No.: WO2009/027634
PCT Pub. Date: Mar. 5, 2009

(65) Prior Publication Data
US 2011/0117223 A1  May 19, 2011

(30) Foreign Application Priority Data
Aug. 24, 2007 (GB) .................................. 0716605.1

(51) Int. Cl.
| | |
|---|---|
| *A61K 36/61* | (2006.01) |
| *A61K 36/00* | (2006.01) |
| *A61K 36/53* | (2006.01) |
| *A61K 31/045* | (2006.01) |
| *A61K 31/05* | (2006.01) |
| *A61K 31/155* | (2006.01) |
| *A61K 45/06* | (2006.01) |

(52) U.S. Cl.
CPC ............ *A61K 36/53* (2013.01); *A61K 31/045* (2013.01); *A61K 31/05* (2013.01); *A61K 31/155* (2013.01); *A61K 36/61* (2013.01); *A61K 45/06* (2013.01)

(58) Field of Classification Search
CPC ......... A61K 31/00; A61K 31/04; A61K 36/61
USPC ....................................................... 424/742
See application file for complete search history.

(56) References Cited

U.S. PATENT DOCUMENTS

| | | | | |
|---|---|---|---|---|
| 6,022,551 A * | 2/2000 | Jampani et al. | ............... | 424/405 |
| 2006/0105000 A1 * | 5/2006 | Friedman | ....................... | 424/400 |

FOREIGN PATENT DOCUMENTS

WO  WO-2004/080399 A2  9/2004

OTHER PUBLICATIONS

Filoche et al, "Antimicrobial effects of essential oils in combination with chlorhexidine digluconate" Oral Microbiology and Immunology, 2005, 20: 221-225.*
Nostro et al., "Effects of oregano, carvacrol and thymol on *Staphylococcus aureus* and *Staphylococcus epidermidis* biofilms", Journal of Medical Microbiology (2007), 56, 519-523.*
Adams et al., "Evaluation of a 2% of a chlorhexidine gluconate in 70% isopropyl alcohol skin disinfectant" Journal of Hospital Infection (2005), 61, 287-290.*
Schelz et. al. "Antimicrobial and antiplasmid activities of essential oil", Fitoterapia 77 (2006), 279-285.*
Adams, D. et al. "Evaluation of a 2% chlorhexidine gluconate in 70% isopropyl alcohol skin disinfectant" *Journal of Hospital Infection*, 2005, 61:287-290.
Al-Shuneigat, J. et al. "Effects of a topical essential oil-containing formulation on biofilm-forming coagulase-negative staphylococci" *Letters in Applied Microbiology*, 2005, 41:52-55.
Filoche, S.K. et al. "Antimicrobial effects of essential oils in combination with chlorhexidine digluconate" *Oral Microbiology and Immunology*, 2005, 20:221-225.
Karpanen, T.J. et al. "Antimicrobial efficacy of chlorhexidine digluconate alone and in combination with eucalyptus oil, tea tree oil, and thymol against planktonic and biofilm cultures of *Staphylococcus epidermidis*" *Journal of Antimicrobial Chemotherapy*, 2008, 62:1031-1036.
Lafforgue, C. et al. "Rapid communication: Percutaneous absorption of a chlorhexidine digluconate solution" *International Journal of Pharmaceutics*, 1997, 147:243-246.
Reichling, J. et al. "In vitro studies on release and human skin permeation of Australian tea tree oil (TTO) from topical formulations" *European Journal of Pharmaceutics and Biopharmaceutics*, 2006, 64:222-228.
Williams, A.C. et al. "Penetration enhancers" *Advanced Drug Delivery Reviews*, 2004, 56:603-618.

* cited by examiner

*Primary Examiner* — Chris R Tate
*Assistant Examiner* — Deborah Davis
(74) *Attorney, Agent, or Firm* — Saliwanchik, Lloyd & Eisenschenk

(57) ABSTRACT

The present invention is based on the surprising antiseptic nature of chlorhexidine when combined with essential oils. It has been found that chlorhexidine, combined with an essential oil, is surprisingly effective at penetrating the skin surface and providing an antiseptic effect within the skin. It has also been found that a combination of chlorhexidine and eucalyptus oil is surprisingly effective as an antimicrobial against *Staphylococcus epidermidis*.

30 Claims, 2 Drawing Sheets

A

B

ANTISEPTICS

CROSS-REFERENCE TO RELATED APPLICATION

This application is the U.S. national stage application of International Patent Application No. PCT/GB2008/002832, filed Aug. 21, 2008, the disclosure of which is hereby incorporated by reference in its entirety, including all figures, tables and amino acid and nucleic acid sequences.

FIELD OF THE INVENTION

The present invention relates to antiseptic compositions that are particularly useful for antisepsis of the skin.

BACKGROUND TO THE INVENTION

Incision of human skin is common practice in the clinical environment, for example during surgery, taking blood or on insertion of intravascular devices such as catheters. Hospital acquired infections are frequent complications following incision of the skin, particularly when intravascular devices are inserted, and are commonly associated with skin microorganisms, for example *Staphylococcus epidermidis* (Richards, et al., 2000; Pfaller, et al., 1999; Rupp and Archer 1994).

Several factors contribute to establishment of the infection, for example inadequate skin disinfection prior to skin penetration (Lafforgue, at al., 1997; Traore, et al., 2000; Langgartner, at al., 2004) and the emergence of resistant microorganisms within the clinical setting, often due to the wide use of antimicrobial agents including antibiotics, antiseptics and other biocides (Koljalq, at al., 2002; Fraise, 2002; Block and Furman, 2002).

Microorganisms may exist as microcolonies within the skin or as biofilms in situ on intravascular devices, for example on the surface of a catheter, and are therefore more resistant to higher concentrations of antimicrobials compared to microorganisms in suspension (Rupp and Archer, 1994; Gristina, at al., 1989; Saginur, et al., 2006).

Many antimicrobials are known for the treatment of skin infections. For example, chlorhexidine is known to have a broad range of antimicrobial activity, with rapid action, suitable for skin preparation prior to invasive procedures such as CVC insertion (McDonnell and Russell, 1999).

Some essential oils have also been shown to have antimicrobial activity with efficacy against bacteria, yeast and viruses (Cowan, 1999; Karpanen, et al., 2006). Tea tree oil (TTO) has also been shown to be effective in eradicating MRSA colonization (Al-Shuneigat, at al., 2005; Dryden, at al., 2004; Caelli, et al., 2000) and reducing microbial contamination of hands (Messager, et al., 2005). Other essential oils including eucalyptus and thymol have also been investigated for their potential clinical applications; thymol has been shown to have anti-inflammatory properties and increase wound healing in burns (Dursun, et al., 2003) and eucalyptus was found to improve healing of necrotic ulcers (Warnke, et al., 2006).

The combination of an essential oil with chlorhexidine digluconate is known. Antimicrobial effects of combinations of essential oils with chlorhexidine digluconate against oral pathogens *Streptococcus mutans* and *Lactobacillus plantarum* have been studied (Flioche, et al., 2005), with a view to development of novel anticaries treatments. US 2006/0105000 describes compositions for treating infected skin and mucosal membranes comprising an anti-microbial agent and an essential oil. Chlorhexidine gluconate was used as the anti-microbial agent in a mucositis mouthwash, an anal fissure gel and a pressure sore wash.

Despite the wide range of available antimicrobials, a number of antimicrobials, including chlorhexidine, are known to show poor permeability into the skin, so bacteria deeper in the skin or beneath the surface of the skin and in the hair follicles often remain unaffected by current methods of skin disinfection. Therefore infections, in particular those in the skin, remain a problem, as the antimicrobial cannot penetrate the skin.

New methods for delivering skin antiseptics have been explored, such as liposomes, microparticles and nanoparticles, which would provide targeted and controlled release of antimicrobial agents (Constant, et al., 2006). Essential oils have also been studied as skin permeation enhancers (Biruss, et al., 2007; Reichlich, et al., 2006; Fang, et al., 2004). However the effectiveness of essential oils as permeation enhancers is limited because the ability of an essential oil to increase permeation through the skin is drug specific. Therefore, there remains a general need for improved antimicrobials, in particular for methods and products for preventing and treating sub-cutaneous infections.

SUMMARY OF THE INVENTION

The present invention is based on the discovery that chlorhexidine, when used in combination with at least one essential oil, shows enhanced antimicrobial properties and permeation of the skin, with a surprising increase in skin permeation. The specific combination of an essential oil and chlorhexidine is therefore useful for preventing and/or treating infections within the skin layer (for example, the dermis) in particular those resulting from invasive medical procedures, e.g. insertion of catheters.

The present invention is also based on the finding that chlorhexidine, when used in combination with eucalyptus oil, shows surprisingly good antimicrobial activity against *S. epidermidis* and biofilms of *S. epidermidis*. This combination is therefore useful for preventing and/or treating infections from *S. epidermidis*, in particular from invasive medical procedures, e.g. insertion of catheters.

Accordingly, a first aspect of the present invention provides the use of chlorhexidine in combination with an essential oil in the manufacture of a medicament for the prevention and/or treatment of an infection in the skin below the stratum corneum.

A second aspect of the present invention provides the use of chlorhexidine in combination with eucalyptus oil in the manufacture of a medicament for the prevention and/or treatment of infection from *S. epidermidis*.

Another aspect of the present invention relates to a combination of chlorhexidine and an essential oil for use in the prevention and/or treatment of an infection in the skin below the stratum corneum.

Another aspect of the present invention relates to a combination of chlorhexidine and eucalyptus oil for use in the prevention and/or treatment of infection from *S. epidermidis*.

Another aspect of the present invention relates to a method for the prevention and/or treatment of an infection in the skin, below the stratum corneum, comprising contacting the skin with a combination of chlorhexidine and an essential oil.

Another aspect of the present invention relates to a method for the prevention and/or treatment of infection from

*S. epidermidis* comprising contacting the *S. epidermidis* with a combination of chlorhexidine and eucalyptus oil.

BRIEF DESCRIPTION OF THE FIGURE

The invention is described with reference to the following figures wherein.

DETAILED DESCRIPTION OF THE INVENTION

Figure 1:
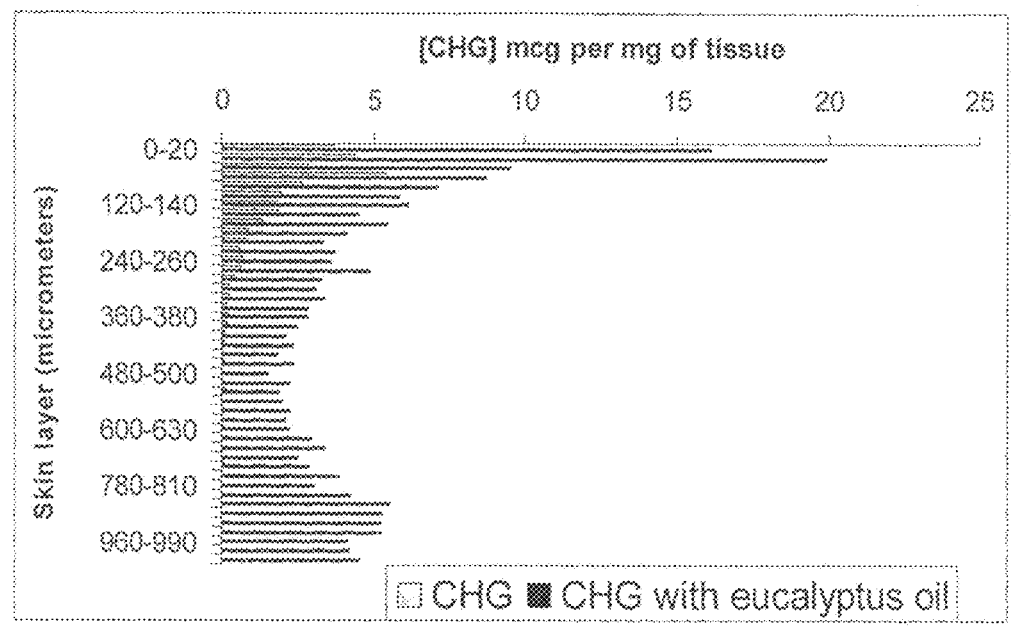
FIG. 1 is a graph showing the concentration of CHG (μg) extracted from the skin at various depths following skin permeation studies of 2% (w/v) CHG with or without 50% (v/v) eucalyptus oil in full thickness human skin (the results are adjusted to the weight of the skin sample)

The following preferences may be combined with one another, where appropriate.

Essential Oil

Essential oils are known in the art and the term "essential oil" is to be given its usual meaning. For the avoidance of doubt, essential oils are volatile mixtures of terpenes and oxygenated compounds such as alcohols, aldehydes, ketones, esters and ethers, that are derived from plant material. These are described, for example, in Williams, et al., 2004. Essential oils can be produced according to any technique known in the art; the most common techniques involve distillation, cold pressing or solvent extraction of the essential oil from raw plant material.

In embodiments of the present invention that involve the use of chlorhexidine and at least one essential oil, a single essential oil may be used, or a combination of different essential oils. In a preferred embodiment, a single essential oil is used. Most preferably, this is eucalyptus oil.

Examples of essential oils include, but are not limited to, eucalyptus, thymol, tea-tree oil, chenopodium, ylang ylang, cinnamon oil, manuka oil, menthol, grapefruit oil, arnica oil, fennel oil, geranium oil, lavender oil, lemon oil, spearmint oil, pine oil, peppermint oil, basil oil and rosemary oil.

Preferably the essential oil is thymol, eucalyptus oil or tea-tree oil.

Regarding antimicrobial properties, when used in combination with chlorhexidine, the essential oil is most preferably eucalyptus oil.

The most preferred combination according to the invention is chlorhexidine gluconate (CHG) and eucalyptus oil.

Chlorhexidine

Chlorhexidine (CAS number 55-56-1) is a chemical antiseptic that is well-known in the art. Chlorhexidine can be used in its free base form or in a salt form. The salt is preferably a pharmaceutically acceptable salt, a number of which are well known in the art, most preferably chlorhexidine digluconate (CAS number 18472-51-0), referred to herein as "CHG".

Infection

It has been found that a combination of chlorhexidine and an essential oil is surprisingly effective at penetrating into the skin, thereby providing an antimicrobial effect within the skin. Therefore, a first aspect of the present invention relates to the use of chlorhexidine in combination with an essential oil in the manufacture of a medicament for the prevention and/or treatment of infection in the skin. The term "in the skin" refers to an infection that is not on the surface of the skin, but is within the skin organ, i.e. below the surface layer. The infection may therefore be any form of infection that occurs in the skin beneath the upper layer of the skin, known as the Stratum Corneum.

Preferably, the infection in the skin is caused by one or more microorganisms arising on and within the skin and that are introduced to the deeper layers of the skin beneath the Stratum Corneum by an invasive medical procedure, for example, by introduction of a catheter into the body.

Examples of infections in the skin that may be targeted by the (first aspect of the) present invention include, but are not limited to, localised skin infections (e.g., infection associated with insertion of an intravascular device, for example central venous catheter, peripheral catheter, PD catheter, shunts), acne, skin boils, carbuncles, spots, dermatophyte infections, surgical site infection, ulcers and burns. Preferably, the infection is one associated with insertion of an intravascular device. These infections may originate on the surface of the skin but may extend to cause damage in the deeper layers of the skin.

Microorganisms that cause infections in the skin, and may be targeted by the present invention include, but are not limited to, aerobic and anaerobic Gram-positive cocci (for example *staphylococci, streptococci, enterococci*), aerobic and anaerobic Gram-positive *bacilli* (for example *clostridia, bacillus, propionibacteria*), aerobic and anaerobic Gram-negative cocci (for example *neisseria, veillonella*), aerobic and anaerobic Gram-negative cocci (for example *entrobacteria*, pseudomonads, bacteroides), fungi, yeasts and moulds (for example *candida*, dermatophytes).

Preferably, the infection in the skin, according to the first aspect of the invention, is a *staphylococcal* infection. More preferably, the infection is one caused by *S. epidermidis*.

It has also been found that a combination of chlorhexidine and eucalyptus oil is surprisingly effective as an antimicrobial agent against *S. epidermidis*, specifically. Therefore, a second aspect of the present invention relates to the use of a combination of chlorhexidine and eucalyptus oil, in the manufacture of a medicament for the prevention and/or treatment of infection from *Staphylococcus epidermidis* (*S. epidermidis*). *S. epidermidis* is a Gram-positive bacterium that occurs frequently on and in the skin of humans and animals. Several strains of *S. epidermidis* form microcolonies in the skin and protective biofilms on devices such as intravenous catheters. A combination of chlorhexidine and eucalyptus oil is therefore effective at preventing and treating biofilms of *S. epidermidis*. The term "biofilm" is well-known in the art and is to be given its usual meaning. For the avoidance of doubt, a biofilm is a structured community of microorganisms (in this case, *S. epidermidis*) within a self-developed polymeric matrix, on a living or inert, abiotic surface. Preferably, the surface is abiotic, more preferably it is a solid surface. Most preferably, the solid surface is a catheter, more preferably an intravenous catheter such as a Central Venous Catheter. The prevention or reduction of a biofilm on a catheter will prevent or treat an infection in a patient that is caused by the biofilm bacteria.

The combination of chlorhexidine and eucalyptus oil described herein can be used to prevent and/or treat *S. epidermidis* infection, by contacting the *S. epidermidis* with the chlorhexidine and eucalyptus oil. Preferably, the chlorhexidine/eucalyptus oil combination is used to prevent and/or treat strains of *S. epidermidis* found on and within the skin and which may cause infection. Preferably the *S.*

*epidermidis* strain is a biofilm-forming strain, for example, RP62A. Preferably the infection caused by *S. epidermidis* is an infection of the skin. The combination of chlorhexidine and eucalyptus oil has been found by the present inventors to have synergistic antimicrobial activity against biofilms of *S. epidermidis* that is surprisingly enhanced when compared to the antimicrobial activities of chlorhexidine and eucalyptus oil alone.

A skin infection, according to either the first aspect or a preferred embodiment of the second aspect of the invention, is one which occurs in skin that is exposed to form the outer surface of the body. This external skin does not include, for example, internal membranes such as skin or mucous membranes which may occur, for example, in the mouth or nasal passages, for example buccal membranes, the tongue and gums. For the avoidance of doubt, the term skin does not include oral epithelial membranes.

In a preferred embodiment, the skin that is contacted with a composition of the invention is intact, i.e. not broken, cut, split, torn, burnt or otherwise wounded. For the avoidance of doubt, intact skin refers to an intact stratum corneum, i.e. where the skin is sealed. It should be noted that skin that is in the process of healing from a wound or cut is considered to be "intact" once the skin cells have sealed the wound bed, thereby providing a new, intact, stratum corneum. It should further be noted that, when a catheter is inserted through the skin, the skin will often grow to seal the catheter in place. The skin is therefore sealed and this is within the scope of the term "intact skin".

A composition of the invention can penetrate through the upper layer of skin to treat or prevent an infection within the skin. Therefore, in a preferred embodiment, a composition of the invention is for external, topical use only.

The skilled person will understand that preventing or treating an infection in one area, i.e. the skin, may prevent a more serious infection, or an infection in a different area (caused by the skin infection). Such secondary infections are often referred to as hospital acquired infections or nosocomial infections. For example, preventing or treating a localised infection such as a skin infection will reduce the likelihood of a systemic infection occurring. A common systemic infection that can be caused by an initial, localised infection is an infection of the blood, often referred to as blood poisoning or blood sepsis. Therefore, preventing a localised infection according to the invention will have the further benefit of reducing the incidence of a more serious infection such as a systemic infection. An example is the insertion of a catheter into a patient; an initial infection is often of the skin but, unless treated, this infection can rapidly become more severe and can cause blood poisoning. The compositions of the present invention are effective at reducing the occurrence of these secondary infections.

Skin Structure

Skin has two main layers, the epidermis and the dermis. The thickness of these layers varies between different body sites.

The epidermis is the outmost layer and the main barrier for drug absorption. It is approximately 50 to 100 µm thick, of which the Stratum Corneum (the main barrier layer) is approximately 10 µm thick. The epidermis does not contain blood vessels and is comprised mainly of keratinocytes. There are five distinctive layers: the stratum corneum, stratum lucidum, stratum granulosum, stratum spinosum, and stratum basale.

The dermis is the layer beneath the epidermis and is approximately 1000 µm thick, but may vary between 100 µm and 3000 µm thick depending on the body site. It consists mainly of connective tissue and contains blood, lymphatic vessels and sensory receptors. It also contains hair follicles, sebaceous glands and sudoriferous glands. There are two types of sweat producing glands: apocrine, which opens into the hair follicle canal, and eccrine, which opens directly to the skin surface.

Below the dermis is the hypodermis or subcutaneous layer which contains adipose tissue.

The chlorhexidine and essential oil combinations described herein having good permeation properties must be capable of permeating through the stratum corneum, the major barrier for antiseptic skin permeation, and/or be capable of permeating into the hair follicles. The hair follicles may harbour bacteria which are not eradicated by current skin antisepsis procedures and may cause infection during invasive procedures.

The present inventors have discovered that combinations of chlorhexidine, preferably CHG and at least one essential oil, preferably eucalyptus oil, exhibit excellent permeation properties not seen or studied before. Accordingly, as described above, the first aspect of the present invention relates to the use of chlorhexidine in combination with at least one essential oil in the manufacture of the medicament for the prevention of an infection of the skin at certain depths in the skin layer.

The infection to be prevented and/or treated according to the first aspect of the invention occurs below the Stratum Corneum.

In one embodiment, the infection to be prevented and/or treated occurs at a depth of up to 3000 µm in the skin layer, preferably at a depth of up to 2000 µm, and more preferably at a depth of up to 1000 µm.

In another embodiment, the infection to be prevented and/or treated occurs at a depth of greater than 100 µm in the skin layer, preferably a depth of greater than 480 µm.

The infection to be prevented and/or treated preferably occurs at a depth of between 100 µm and 3000 µm of the skin layer. In one embodiment the infection to be prevented and/or treated occurs at a depth of between 480 µm and 3000 µm of the skin layer. In one embodiment the infection to be prevented and/or treated occurs at a depth of between 480 µm and 1000 µm of the skin layer. The present inventors have further found that, unexpectedly, the concentration of CHG from the combination of CHG and at least one essential oil increases with increasing depth beyond a depth of 480 µm in the skin layer. Permeation of the combination of CHG and at least one essential oil to a depth beyond 480 µm is surprisingly good.

In another embodiment, the infection to be prevented and/or treated occurs in the dermis.

In another embodiment, the infection to be prevented and/or treated occurs in the hair follicle.

Combinations

In the first aspect of the invention, chlorhexidine can be used in combination with any essential oil. The essential oil may be any of those described above, preferably thymol, eucalyptus oil, or tea-tree oil, and most preferably eucalyptus oil. Chlorhexidine may be combined with any one essential oil, or with a combination of different essential oils. In a preferred embodiment, chlorhexidine is combined with a single essential oil. Most preferably, this is eucalyptus oil.

In the second aspect of the invention, chlorhexidine is combined specifically with eucalyptus oil. In both aspects of the invention the combination of chlorhexidine with an essential oil may further be combined with other pharmaceutically acceptable ingredients, as described below. A preferred additional ingredient is isopropyl alcohol (IPA).

In a preferred embodiment, the chlorhexidine and essential oil, and optionally IPA, are the only antimicrobial agents that are used, i.e. no other antimicrobial agents are required in a composition according to the invention. Preferably, the only active ingredients, i.e. the only antimicrobial ingredients, in a composition according to the first aspect of the invention are chlorhexidine, an essential oil and, optionally, IPA. Similarly, according to the second aspect of the invention, a preferred embodiment provides a composition wherein the only active, i.e. antimicrobial, ingredients are chlorhexidine, eucalyptus oil and, optionally, IPA.

Treatment and Prevention

The first aspect of the invention provides the combination of chlorhexidine and an essential oil, preferably eucalyptus oil, that can be used in the manufacture of a medicament for the prevention and/or treatment of an infection in the skin, preferably prevention.

The second aspect of the invention provides the use of chlorhexidine and eucalyptus oil in preventing and/or treating an *S. epidermidis* infection.

The term "prevention" as used herein in the context of preventing an infection, pertains to the use with patients who have not yet developed the condition, but who are at risk of developing the condition, to prevent a condition occurring. For example, prevention includes the prophylaxis of an infection of the skin, reducing the incidence of skin infection, etc. Prevention of infection also includes sterilization. This preferably involves application of the chlorhexidine and essential oil combination to an area of skin to eliminate microorganisms from that area of skin; in the first aspect of the invention, microorganisms in the skin (below the stratum corneum) will be eliminated, while in the second aspect of the invention, *S. epidermidis* will be eliminated, both in and on the skin.

Preferably, the combination according to the first or second aspect of the invention is used prior to invasive surgery to prevent potential infection by microorganisms from above the skin surface, including microorganisms present on surgical apparatus, being introduced below the skin surface during surgery.

The term "treatment", as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, alleviation of symptoms of the condition, amelioration of the condition, and cure of the condition.

Preferably, the combination of chlorhexidine and an essential oil is applied to the outer surface of the skin and allowed to permeate into the skin layer. Preferably the combination of chlorhexidine and an essential oil permeates into the dermis and/or the hair follicles. If the combination of chlorhexidine and an essential oil is used to prevent a skin infection in a patient about to undergo an invasive medical procedure, e.g., insertion of a catheter, the combination should be applied to the skin of the patient prior to the procedure.

The term "therapeutically-effective amount", as used herein, pertains to that amount of an active compound, or a material, composition or dosage form comprising an active compound, which is effective for producing some desired therapeutic effect, including prevention, commensurate with a reasonable benefit/risk ratio, when administered in accordance with a desired treatment regimen.

For the avoidance of doubt, in one embodiment of the invention, a method of preventing or treating an infection in the skin comprises contacting the skin with chlorhexidine and an essential oil, preferably eucalyptus oil. In one embodiment, the chlorhexidine and essential oil are applied simultaneously. In this embodiment, the chlorhexidine and eucalyptus oil can be applied in or on a woven or non-woven material. For example, a dressing, sponge, bandage, plaster or similar material, that comprises both the chlorhexidine and essential oil, can be used to prevent or treat an infection in the skin. Preferably, the composition is applied using an applicator device. A suitable applicator device typically comprises means for retaining the composition (until application is desired) and means for applying the composition to the skin. The means for retaining the composition is preferably a container such as a tube or ampoule. The means for applying the composition to the skin is preferably a sponge, more preferably a foam sponge. Suitable applicator devices are commercially available from Insight Health Limited, UK.

In an alternative embodiment, the chlorhexidine and essential oil are applied sequentially. Preferably, when applied sequentially, the chlorhexidine is applied to the skin and subsequently, the essential oil is applied. In this embodiment, the essential oil is preferably applied by a material comprising the essential oil, for example a woven or non-woven patch, such as a dressing, sponge bandage, plaster or similar. An applicator device, as described above, can be used to apply the chlorhexidine and/or the essential oil.

The second aspect of the invention relates to the use of chlorhexidine and eucalyptus oil as a biocide against *S. epidermidis*. A preferred embodiment comprises a woven or non-woven material, for example a sponge, towel, towelette, wipe, cloth or similar, which comprises chlorhexidine and eucalyptus oil. This material can be used to contact the *S. epidermidis* with the chlorhexidine and eucalyptus oil and provide the biocidal effect. Preferably, the woven or non-woven material is a hard-surface wipe, more preferably a woven hard-surface wipe.

Dosage

It will be appreciated by one of skill in the art that appropriate dosages of the chlorhexidine and essential oil components can vary from patient to patient. Determining the optimal dosage will generally involve the balancing of the level of therapeutic benefit against any risk of deleterious side-effects. The selected dosage level will depend on a variety of factors including, but not limited to, the activity of the particular composition, the route of the administration, the rate of excretion of the compound, the duration of the treatment, other drugs, compounds, and/or materials used in combination, the severity of the condition, and the species, sex, age, weight, condition, general health, and prior medical history of the patient. The amount of the compounds and route of the administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment or prevention. Methods of determining the most effective means and dosage of administration are well known to those of skill in the art will vary with the formulation used for therapy, the purpose of the therapy, the target infection being treated, and the subject being treated. Single or multiple administrations can be carried out with the dose level and pattern being selected by the treating physician, veterinarian, or clinician.

The chlorhexidine and essential oil combination are administered in a therapeutically-effective amount. The amount of chlorhexidine, preferably CHG, is preferably in the range of from 0.1% to 5% by weight (w/v), more preferably 0.5% to 4% by weight, yet more preferably 0.5% to 2.5% by weight, most preferably 2% by weight. The amount of essential oil is preferably in the range of from 5% to 60% by volume (v/v) of the composition, more preferably 10% to 50% by volume, yet more preferably 10% to 30% by volume, and most preferably 10% to 16% by volume, for example 10% by volume. Experiments have indicated that 10% (v/v) eucalyptus oil is comparable to 50% (v/v) eucalyptus oil in the ability to enhance delivery of CHG through the skin. A suitable dose of the chlorhexidine and essential oil combination is preferably 2% by weight of chlorhexidine and 50% by volume of essential oil, more preferably 2% by weight of chlorhexidine and 30% by volume of essential oil, and preferably 2% by weight of chlorhexidine and 10% or 16% by volume of essential oil.

Where chlorhexidine digluconate is used as a salt, ester, amide, prodrug, or the like, the amount administered is calculated on the basis of the parent compound and so the actual weight to be used is increased proportionately.

The components of the combination may be added simultaneously, or sequentially. In one embodiment, the combination of compounds is applied in a single formulation. A preferred single-formulation composition comprises CHG, eucalyptus oil and isopropyl alcohol.

In a separate embodiment, the chlorhexidine and essential oil are administered separately. More preferably, the chlorhexidine is applied directly to the skin and a material comprising an essential oil is then contacted with the chlorhexidine-coated skin. The material comprising the essential oil may be woven or non-woven, for example a patch, plaster, bandage or dressing. Isopropyl alcohol can optionally be added to the skin before, after, or simultaneously with, the chlorhexidine.

For the avoidance of doubt, a method of preventing or treating an infection according to either aspect of the invention comprises contacting the skin of a patient with a combination of chlorhexidine and an essential oil. Contacting the skin with the chlorhexidine and essential oil will treat or prevent an infection, as detailed herein. In one embodiment, the skin is contacted with the chlorhexidine and essential oil, preferably eucalyptus oil, simultaneously. More preferably, a single formulation comprising the chlorhexidine and essential oil is applied. In a separate embodiment, the method of prevention or treatment of infection comprises contacting the skin of a patient with chlorhexidine and, separately, contacting the chlorhexidine-coated skin with the essential oil, preferably eucalyptus oil. In this embodiment, the chlorhexidine is preferably applied to the skin as a liquid and the essential oil is preferably applied on a woven or non-woven material comprising the essential oil, for example a patch, plaster, bandage or wound dressing. A two-stage application of chlorhexidine followed by essential oil is therefore a preferred embodiment of the invention.

Formulations

While it is possible for the chlorhexidine and essential oil combination to be administered alone, it is preferable to present it as a pharmaceutical formulation (e.g., composition, preparation, medicament) comprising at least the combination of chlorhexidine with at least one essential oil, as defined above, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents. The formulation may further comprise other active agents for example other therapeutic or prophylactic agents.

A preferred active agent for inclusion in a composition according to the first and second aspect of the invention is isopropyl alcohol (IUPAC name: Propan-2-ol). A most preferred composition therefore comprises, and optionally consists essentially only of, CHG, eucalyptus oil and isopropyl alcohol. The IPA can be present at any effective level, i.e. at any level that is effective as an antimicrobial. A preferred amount is 50% to 90% (v/v), more preferably 60% to 80% (v/v) and most preferably 70% (v/v) IPA in the composition. A preferred composition therefore comprises 2% (w/v) CHG, 70% (v/v) IPA and 10% (v/v) eucalyptus oil. A composition comprising isopropyl alcohol is particularly advantageous as it provides a fast-acting anti-microbial effect (due to the isopropyl alcohol) and a prolonged, sustained anti-microbial effect (due to the chlorhexidine and essential oil). This combination has been found to be effective; this is particularly surprising because it has previously been suggested that isopropyl alcohol inhibits the permeation of chlorhexidine, in particular CHG, into the skin. The present inventor has found that the presence of an essential oil, in particular eucalyptus oil, removes this inhibition of penetration, as detailed in the Examples and FIG. 2.

The term "pharmaceutically acceptable" as used herein pertains to compounds, ingredients, materials, compositions, dosage forms, etc., which are, within the scope of the sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Suitable carriers, diluents, excipients, etc. can be found in standard pharmaceutical texts, for example, Remington's Pharmaceutical Sciences, $18^{th}$ edition, Mack Publishing Company, Easton, Pa., 1990; and Handbook of Pharmaceutical Excipients, $2^{nd}$ edition, 1994.

The formulations may be prepared by any methods well known in the art of pharmacy. Such methods include the step of bringing into association the active compound with a carrier which constitutes one or more accessory ingredients. In general, the formulations are prepared by uniformly and intimately bringing into association the active compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

A formulation according to the invention is preferably a topical formulation. Formulations may suitably be in the form of liquids, solutions (e.g., aqueous, non-aqueous), suspensions (e.g., aqueous, non-aqueous), emulsions (e.g., oil-in-water, water-in-oil), gels, pastes, ointments, creams, lotions, oils, foams, sprays, mists or aerosols. Preferably, the formulation is an emulsion. More preferably, the formulation is an emulsion and is supplied in a single formulation.

Formulations may suitably be provided as a patch, adhesive plaster, bandage, dressing, or the like which is impregnated with one or more active compounds and optionally one or more other pharmaceutically acceptable ingredients, including, for example, penetration, permeation, and absorption enhancers other than an essential oil. Formulations may also suitably be provided in the form of a depot or reservoir. Preferably, chlorhexidine is applied to the skin topically, followed by material, preferably a patch and more preferably a biopatch, comprising the at least one essential oil.

The chlorhexidine and essential oil combination may be dissolved in, suspended in, or admixed with one or more other pharmaceutically acceptable ingredients.

Formulations suitable for transdermal administration include gels, pastes, ointments, creams, lotions, and oils, as well as patches, adhesive plasters, bandages, dressings, depots, and reservoirs.

Ointments are typically prepared from the chlorhexidine and essential oil combination and a paraffinic or water-miscible ointment base.

Creams are typically prepared from the chlorhexidine and essential oil combination and an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active compound through the skin or other affected areas, other than an essential oil. Examples of such dermal penetration enhancers include dimethylsulfoxide and related analogues.

Emulsions are typically prepared from chlorhexidine, preferably CHG, and an oily phase, which may optionally comprise merely an emulsifier (otherwise known as an emulgent), or it may comprises a mixture of at least one emulsifier with a fat or oil or with both a fat and an oil. Preferably the oily phase comprises at least one essential oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostarate and sodium lauryl sulphate. The choice of suitable oils or fats for the formulation is based on achieving the desired cosmetic properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or disbasic alky esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

The invention will now be described with the following non-limiting examples.

BIOLOGICAL EXAMPLES (1) Antimicrobial Studies
Organism and Preparation of Bacterial Biofilm S. epidermidis RP62A was used for its ability to produce a biofilm (Sadovskaya, at al., 2005). Bacteria were stored on beads (MicroBank, Pro-Lab Diagnostics, Cheshire, UK) at −70° C. until required. The ability of the strain to produce slime was confirmed by culturing the bacteria on Congo Red agar (Freeman, at al., 1989). For producing the microbial biofilms, the strains were first inoculated onto Muller-Hinton agar (MHA) (Oxoid, Basingstoke, UK) and incubated in air at 37° C. for 18-20 hours. Ten colonies from the culture plate were suspended into sterile phosphate buffered saline (PBS, Sigma, Dorset, UK). The bacterial concentration was adjusted to $1\times10^8$ cfu/mL by diluting the culture with sterile PBS and measuring the OD at 570 nm (calibration curve for S. epidermidis cfu against OD at 570 nm were performed prior to the study, data not shown). The suspension was further diluted with Muller-Hinton broth (MHB) supplemented with 2% (w/v) glucose (Fisher Scientific, Leicester, UK) to obtain inocula containing $1\times10^5$ cfu/mL. Two hundred µL of the bacterial suspension were aliquoted into wells of white walled, clear bottom, tissue culture treated 96-well microtitre plate (Corning Incorporated, NY, USA). The wells in the last column of the plate served as a control, and contained 200 µL of MHB supplemented with 2% (w/v) glucose only. Microtitre plates were incubated in air at 37° C. for 48 hours.

Preparation of Test Inoculum for Assessment of Antimicrobial Efficacy by Suspension Assay Test inocula for the suspension assay were prepared by suspending 10 colonies of S. epidermidis RP62A from an overnight culture on MHA into sterile PBS. The bacterial concentration was adjusted to $1\times10^8$ cfu/mL by diluting the culture with sterile PBS and measuring the OD at 570 nm (calibration curve for S. epidermidis cfu against OD at 570 nm were performed prior to the study, data not shown). The suspension was further diluted with MHB to obtain inocula containing $1\times10^7$ cfu/mL for synergy assays or $1\times10^6$ cfu/ml for testing antimicrobial activity of CHG and oils alone in suspension.

Preparation of Antimicrobial Agents

Aqueous chlorhexidine digluconate (CHG), tea tree oil (TTO), eucalyptus oil (EO) and thymol (all from Sigma-Aldrich) were diluted with MHB to obtain stock solution of 512 mg/mL for essential oils and 512 µg/mL for CHG. Five percent (v/v) dimethylsulphoxide (DMSO) (Sigma-Aldrich) was added to the stocks of essential oils to enhance their solubility of the oils in suspension.

Calibration Curve for ATP Bioluminescence and Bacterial Colony Count

Prior to antimicrobial susceptibility studies, a standard curve for relative light units (RLU) versus bacterial cfu/mL was performed. S. epidermidis was grown with MHB supplemented with 2% (w/v) glucose in a 96-well microtitre plate as described previously to obtain bacterial biofilms. The wells of the microtitre plate with established bacterial biofilms were washed three times with sterile PBS and biofilms were removed from the wells by using "a scrape and wash method" (Adams, 2006). In brief, each well was filled with 200 µL of sterile PBS and, with a sterile pipette tip, the wall of each well was scraped approximately 10 times and the bottom scraped horizontally, vertically and cross-wise in each direction 10 times. The suspension was removed and collected into a sterile Eppendorf tube and the procedure repeated a further 4 times to obtain a final volume of 1000 µL per tube. The procedure was performed on three wells separately. The suspensions were mixed by vortexing and serial dilutions were performed in sterile PBS. 100 µL of the neat suspension and $10^{-1}$ to $10^{-5}$ dilutions were aliquoted onto wells of a white-walled, clear bottom microtitre plate. 100 microliters of bactolyse were added into each well. The plate was then floated on a water bath sonicator and the plate was sonicated at 50 Hz for 30 minutes to lyse the cells and release the bacterial ATP. Twenty µL of luciferase where added into each well and luminescence read by a luminometer. The bacterial cfu in each suspension and dilution were established by the drop count method. The results were expressed as cfu against RLU.

Antimicrobial Activity of TTO, EO, Thymol and CHG Against *S. epidermidis* in Suspension Minimum inhibitory concentration (MIC) and minimum bacterial concentration (MBC) of aqueous CHG, TTO, EO and thymol were performed by microbroth dilution assay (NCCLS, 1997). In brief, the antimicrobial agents were aliquoted into the first column in clear, round bottom, 96-well microtitre plates (Serowell Bibby-Sterlin, Staffordshire, UK) and serial double dilutions were performed with MHB in the successive columns. The last column served as a control containing MHB and no antimicrobial agent. Antimicrobial activity of 5% (v/v) to 0.6% (v/v) DMSO was tested on separate microtitre plate alongside the assay. All the wells were inoculated with 100 µl of *S. epidermidis* suspension containing 1×10*6 cfu/mL and the plates were incubated in air at 37° C. for 20 hours. Minimum bactericidal concentrations were determined by removing the suspension from the clear wells into MHA, spread with a sterile spreader and incubating the plates in air at 37° C. for 18-20 hours. The assay was performed in triplicate.

Antimicrobial Activity of CHG, TTO, EO and Thymol Against *S. epidermidis* Biofilm Microtitre plates containing *S. epidermidis* RP62A biofilm were washed once with sterile PBS to remove any unbound bacteria. Antimicrobial agents were diluted with MHB to obtain CHG concentrations of 128 µg/mL to 0.25 µg/mL and essential oil concentrations of 256 mg/mL to 0.5 mg/mL. Two hundred and fifty microliters of the antimicrobial compound were added in the wells in triplicate. Columns 11 and 12 served as controls with biofilm with saline alone and clear wells with MHB alone without bacterial biofilm. Antimicrobial activity of 5% (v/v) DMSO against bacterial biofilm was tested alongside the test on a separate plate. Following the incubation of the bacterial biofilms with antimicrobial agent at 37° C. in air for 20 hours, the wells were washed once with sterile PBS and the microbial killing determined by ATP bioluminescence (ViaLight MDA Bioassay kit, Cambrex, Berkshire, UK); In brief, 100 µL of Bactolyse (ViaLight MDA) were added with 100 µl of saline into each well and the plates were sonicated at 50 Hz for 30 minutes to release and lyse the cells in the bacterial biofilm. 50 µl of ATP-monitoring reagent (ViaLight MDA Bioassay kit) were added to each well and luminescence measured. The assay was performed in duplicate.

Antimicrobial Susceptibility of TTO, EO and Thymol in Combination With CHG Against Suspension of *S. epidermidis*

The antimicrobial activity of TTO, EO and thymol in combination with aqueous CHG was assessed in a suspension assay by the checkerboard method (Shin and Lim, 2004). In brief, serial double-dilutions of the antimicrobial compounds were prepared (128 mg/mL to 1 mg/mL for essential oils and 64 µg/mL to 0.5 µg/mL for CHG). 50 microliters of CHG dilutions were pipetted into the columns of a 96-well microtitre plate in diminishing concentrations and 50 microliters of the essential oil were aliquoted into the rows in diminishing concentration. The wells were then inoculated with 10 µl of bacterial suspension containing 10*5 cfu. Columns 10, 11 and 12 served as controls containing nutrient broth and inoculum alone, and antimicrobial compounds separately with the inoculum, respectively. The microtitre plates were incubated in air at 37° C. for 24 hours and the plates inspected for microbial growth to determine the MIC of the compounds alone and in combination. To determine synergistic or antagonistic activity of antimicrobial combinations, the fractional inhibitory concentration (FIC) and FIC index (FICI) was determined using the formulae:

$$FIC = \frac{\text{lowest MIC of antimicrobial agent combination}}{\text{MIC of the antimicrobial agent alone}}$$

$$FICI = FIC \text{ of } OIL + FIC \text{ of } CHG$$

FICI less than 0.5 were regarded as synergistic effect, values between 0.5 to 4.0 as indifference and over 4.0 as antagonistic activity. The assay was performed in duplicate.

Antimicrobial Susceptibility of TTO, EO and Thymol in Combination With CHG Against *S. epidermidis* Biofilm Microtitre plates containing *S. epidermidis* RP62A biofilm was washed once with sterile PBS to remove any unbound bacteria. Antimicrobial agents were diluted with MHB as described above and 125 µl of each of the dilutions were aliquoted into wells in microtitre plates in decreasing concentrations as in checkerboard assay described previously, with the total volume of 250 µl per well to ensure the bacterial biofilms were fully covered. The columns 10, 11 and 12 served as controls and contained antimicrobials compounds alone, and biofilm alone with saline. The plates were incubated in air at 37° C. for 24 hours after which the wells were emptied and the FIC and FICI values were determined by ATP bioluminescence as described previously. The assay was performed in duplicate.

Results

*S. epidermidis* RP62A was confirmed to be the slime-producing strain by producing characteristic black, crusty, colonies on Congo Red agar. Following 48 hour incubation of *S. epidermidis* RP62A in MHB supplemented with 2% (w/v) glucose the bacterial biofilm in each well contained an average of 5.53×10*6 cfu.

Minimum inhibitory concentrations for CHG was 2-fold, tea tree oil 3-fold and eucalyptus oil 5-fold higher against bacteria growing in biofilm (MIC 8 µg/mL, 16 mg/mL and 128 mg/mL respectively) compared to planktonic cells (MIC 2 µg/mL, 2 mg/mL and 4 mg/mL respectively). Thymol MIC values were 2-fold lower against biofilms compared to planktonic cells (4 mg/mL and 1 mg/mL, respectively). The bacterial biofilm was eradicated by CHG and all 3 essential oils, with MBC/biofilm eradicating concentration of CHG, thymol, TTO and eucalyptus 32 µg/mL, 2 mg/mL, 64 mg/mL and 256 mg/mL, respectively (Tables 1 and 2).

It has been found that combining CHG with TTO, eucalyptus oil or thymol does not interfere with the antimicrobial activity of CHG or the oil. Furthermore it has been found that CHG combined with EO enhanced synergistically their activity against *S. epidermidis* growing in biofilm (Table 2). In addition, TTO and CHG concentrations required to inhibit biofilm growth were reduced by 2-fold and one-fold respectively, when used in combination (16 mg/mL to 4 mg/mL of TTO, 8 µg/mL to 4 µg/mL of CHG), but thymol in combination with CHG did not affect the concentrations required to inhibit the bacterial growth in biofilm or suspension (TTO 0.5 mg/mL and CHG 8 µg/mL). Five percent (v/v) DMSO, which was used as emulsifier in oil suspensions, did not show antimicrobial activity against *S. epidermidis* in biofilm or suspension.

Table 1 and Table 2 show the antimicrobial activity of eucalyptus oil, tea tree oil and thymol in combination with aqueous chlorhexidine digluconate against *S. epidermidis* RP62A growing in suspension and in biofilm.

TABLE 1

Suspension

| Suspension Combination | MIC of oil (mg/ml) in combination/ alone | FIC of oil | MIC of CHG (µg/ml) in combination/ alone | FIC of CHG | FICI | Result |
|---|---|---|---|---|---|---|
| CHG + Eucalyptus | 4/4 | 1 | 2/2 | 1 | 2 | Indifference |
| CHG + Tea tree oil | 2/2 | 1 | 2/2 | 1 | 2 | Indifference |
| CHG + Thymol | 1/4 | 0.25 | 2/2 | 1 | 1.25 | Indifference |

TABLE 2

Biofilm

| Biofilm Combination | MIC of oil (mg/ml) in combination/ alone | FIC of oil | MIC of CHG (µg/ml) in combination/ alone | FIC of CHG | FICI | Result |
|---|---|---|---|---|---|---|
| CHG + Eucalyptus | 4/32 | 0.125 | 0.25/8 | 0.03125 | 0.15625 | Synergy |
| CHG + Tea tree oil | 4/16 | 0.25 | 4/8 | 0.5 | 0.75 | Indifference |
| CHG + Thymol | 0.5/0.5 | 1 | 8/8 | 1 | 2 | Indifference |

(2) Skin Permeation Studies—CHG+Eucalyptus Oil

Human Skin Samples

Full thickness human skin samples were obtained from patients undergoing breast reduction surgery (The Stephen Kirby Skin Bank, Queen Mary's Hospital, London, UK). Prior to the study full ethical committee approval and written consent from patients donating the tissue was obtained. The full thickness human skin was frozen on the day of excision and stored at −70° C. until the day of investigation.

Franz Diffusion Cells

Vertical diffusion cells (Franz diffusion cells), with an average diffusion surface area of 1.65 cm², were used for skin permeation studies. Phosphate buffered saline (PBS) was used as a receptor fluid, and left overnight in a receptor compartment (approximately volume 29 mls) with circulating water jacket set at 37° C. On the day of investigation the excised skin was thawed in PBS and cut into size to fit Franz diffusion cells (2.9 cm circle across). The skin samples were mounted into Franz diffusion cells and left for 1 hour in the diffusion cells to equilibrate with the receptor fluid prior to commencing the study.

Antimicrobial Agents

Two percent (w/v) chlorhexidine digluconate (CHG) solution was prepared by diluting the 20% (w/v) CHG with sterile distilled water and 0.001% (v/v) Tween 80. Eucalyptus oil with CHG suspension was prepared by diluting the agents with distilled water to obtain final concentration of 50% (v/v) eucalyptus oil, 2% (w/v) CHG and 0.001% (v/v) Tween 80.

Skin Permeation Studies

One milliliter of CHG solution of CHG/eucalyptus oil suspension was aliquoted in triplicate on the surface of the excised human skin on the donor compartment in Franz diffusion cells. The temperature was maintained constant by a circulating water jacket set at 37° C. and the receptor fluid was agitated continuously by magnetic stirrer bar. The receptor fluids were sampled by drawing 1 ml of the fluid every 10 minutes for the first hour, every 30 minutes for the following 7 hours and after 12 and 24 hours. The receptor fluids were replaced after each sample. The samples were filtered and analysed by HPLC.

Section of the Skin Samples

The excised human skins were removed from the Franz diffusion cells following the skin permeation studies and rinsed with PBS. The skins were dried with paper towels, cut into sample 0.5 cm circles across in triplicate, frozen and stored at −70° C. until further investigations. The frozen skin samples were sectioned in 20 µm sections from skin surface to 600 µm depth and 30 µm sections from 600 µm to 1050 µm depth by using a microtome.

Analysis of CHG in Skin Layers

The mobile phase solution for HPLC analysis was used as CHG extractant from skin layers. Each of the 20 µm or 30 µm skin sections were placed into Eppendorf tubes separately and the weight of the skin sections determined by weighing the tubes before and after adding the skin sample. CHG was extracted from the skin samples by aliquoting 1 ml of the extractant into the tubes with skin section and heated in 60° C. water bath for 1 hour, mixed by vortexing and centrifuged for 10 minutes at 6000 g. The samples were filtered and analysed by HPLC.

High-performance Liquid Chromatography (HPLC)

Chlorhexidine digluconate was analysed quantitatively by HPLC. The mobile phase solution for HPLC analysis contained 75:25 methanol:double distilled water, 0.005M sodium heptane sulphonate, 0.1% (v/v) diethylamine and adjusted to pH 4 with glacial acetic acid. The samples were filtered and analysed with HPLC (Agilent 1100) with ODS-2 Hypersil column (5μ particle size) (Thermo Electron Corporation, UK) with a flow rate of 1.2 mls/min, detector wavelength 254 nm.

Results

Following 24 hour skin permeation studies of 2% (w/v) CHG with or without 50% (v/v) eucalyptus oil, and using full thickness human skin, did not show detectable levels of CHG in the receptor fluid. The eucalyptus oil permeated deeper into the skin and at higher concentrations than compared to CHG alone (FIG. 1).

Beyond a depth of about 480 μm the of the skin layer, FIG. 1 shows a surprising increase in CHG concentration with increasing depth up to a skin depth of about 1000 μm when used in combination with eucalyptus oil.

Skin Permeation of CHG With Eucalyptus Oil and Alcohol

The aim of this study was to evaluate the skin permeation of CHG and retention of CHG at the increasing depths of excised human skin following exposure to 2% (w/v) CHG in 70% (v/v) IPA and in combination with eucalyptus oil ("EO").

Materials

Chemicals

Sodium heptane sulphonate, diethylamine (both HPLC grade), phosphate buffered saline (PBS), aqueous 20% (w/v) CHG, eucalyptus oil (EO) (82.9% cineole) and Isopropyl alcohol (IPA) were purchased from Sigma-Aldrich (Dorset, UK). Methanol and glacial acetic acid (all HPLC grade) were purchased from Fisher Scientific (Leicestershire, UK).

Equipment

Agilent 1200 series High Performance Liquid Chromatography (HPLC) was purchased from Agilent Technologies (UK) and the CPS-2 Hypersil reverse phase chromatography column (150×4.6 mm, 5μ particle size) was purchased from Thermo Electron Corporation (UK). Cryotome was purchased from Bright Instruments (Cambs, UK).

Skin Samples

Full thickness human skin samples were obtained from patients undergoing breast reduction surgery (The Stephen Kirby Skin Bank, Queen Mary's Hospital, London, UK) and full ethical committee approval was obtained prior to this study (REC 2002/169). The full thickness human skin was frozen on the day of excision and stored at −70° C. until required.

Methods

Skin Permeation of CHG With EO and IPA

Skin permeation studies were performed with vertical Franz diffusion cells. The receptor compartment was filled with 29 mL of PBS and maintained at 37° C. by a circulating water jacket and agitated by stirring with a magnetic bar. Skin samples were thawed in PBS at room temperature, dried with an absorbent towel and mounted onto Franz diffusion cells with the stratum corneum (SC) uppermost facing the donor compartment. The surface area exposed to the test compound was 3.14 cm2 (2 cm in diameter). All entrapped air was removed between the skin and receptor fluid and the skin was left to equilibrate for 30 min to reach the skin surface temperature of 32° C.

Twenty percent (w/v) aqueous CHG was diluted with distilled water, IPA and DO to obtain the final concentrations of 2% (w/v) CHG in 70% (v/v) IPA and 2% (w/v) CHG with 5%, 10%, 20% and 50% (v/v) EO. Tween 80 [0.1% (v/v)] was added to the test solutions to enhance EO solubility in the vehicle. One milliliter of test solution was spread over the skin surface in the donor compartment and the compartment was sealed with a moisture resistant film to prevent evaporation. One milliliter of receptor fluid was removed every 30 min for 2 h, every hour between 2 to 6 h and at 8 h, 12 h and 24 h. Fluid removed from the receptor compartment was immediately replaced with an equal volume of fresh PBS solution. All samples were filtered through a 0.45 μm nylon filter (Kinesis, UK) and analysed by HPLC. The assay was performed in triplicate.

CHG Quantification by HPLC

The samples were run at room temperature through a reverse phase chromatography column (CPS-2 Hypersil) at a flow rate of 1.2 mL/min for 9 min, with ultraviolet detection at 254 nm. The isocratic mobile phase consisted of methanol:water mixture (75:25) with 0.005 M sodium heptane sulphonate and 0.1% (v/v) diethylamine adjusted to pH 4 with glacial acetic acid. (The method for CHG quantification by HPLC was validated and the level of detection (LOD) and level of quantification (LOQ) were determined prior to the study-data not shown).

CHG Penetration Profile Studies With EO and IPA

The excised full thickness human skin samples mounted onto the Franz diffusion cells were exposed to 2% (w/v) CHG in 70% (v/v) IPA and 2% (w/v) CHG with 50% (v/v) EO (both with 0.1% (v/v) Tween 80) for 2 min, 30 min and 24 h. Two percent (w/v) CHG with 20%, 10% and 5% (v/v) EO with 0.1% (v/v) Tween 80 were evaluated for CHG penetration following 24 h exposure. Following exposure, the skin samples were removed, washed with PBS and dried with an absorbent towel. The skin samples were immediately sprayed with a cryospray (Bright Instruments) and frozen at −20° C. Punch biopsies (7 mm in diameter) were cut from each frozen sample in triplicate and placed onto a cork disc in embedding compound (Bright Instruments, Cambs, UK), The frozen samples were sectioned horizontally with a microtome (Bright Instruments) into 20 μm sections (from the surface to a depth of 600 μm) and 30 μm sections (from depths of 600 to 1500 μm). Each section was placed into an Eppendorf tube and the total weight of each skin sample determined.

Chlorhexidine was extracted from the skin by aliquoting 1 mL of mobile phase solution (75% methanol, 25% distilled water, 0.1% sodium heptane sulphonate, 0.1% diethylamine, pH 4) into skin samples and incubated in water bath at 60° C. for 1 h. The samples were mixed by vortexing and filtered prior to analysis by HPLC. The results were calculated as pg of CHG per mg of skin. Control skin (skin without treatment) was analysed parallel to the test samples. The assay was performed in triplicate.

Statistical Analysis

The data obtained were analysed by a student t-test using INSTAT3 software (Graph pad software version 3.06) with a $p<0.05$ level of significance.

Results

Skin Permeation Studies

Chlorhexidine was not detected in the receptor compartment (LOD 0.0157 μg/mL) during the 24 h permeation study when using skin from two donors. Negligible levels of CHG (less than 0.0016% of the applied dose) were detected during the permeation studies on a $3^{rd}$ donor skin following 24 h exposure to 2% (w/v) CHG in 70% (v/v) IPA and 2% (w/v)

CHG with 50% (v/v) EO.

CHG Skin Penetration Profile Studies

CHG Skin Penetration Following 2 min and 30 min Exposure

The amount of CHG which penetrated and was retained in the skin was significantly higher following treatment with CHG in combination with 50% (w/v) EO compared to CHG in aqueous solution or CHG with 70% (v/v) IPA; after 2 min exposure there was a significant difference in mean CHG concentrations at the deeper layers of the skin when exposed to CHG with 50% (v/v) EO compared to aqueous CHG (300 to 1500 μm depths; p<0.05) with a mean concentration of CHG (and SEM) within the tissues at this depth of 0.0270 μg/mg (±0.0021 μg/mg) tissue following combined antisepsis with CHG/EO and 0.0048 μg/mg (±0.0008 μg/mg) tissue following antisepsis with CHG alone. The differences between CHG/EO and CHG in 70% (v/v) IPA were significant at all skin depths with a mean CHG concentration (and SEM) in the top 100 μm 0.1167 (±0.0313) and 0.0226 (±0.007) for CHG/EO and CHG/IPA respectively.

At 30 min the concentrations of CHG at the all skin depths were significantly higher (p<0.05) with CHG/EO compared to CHG alone or CHG/IPA; at the depths of 300 μm to 1500 μm CHG concentration increased >9.5-fold between CHG/EO and CHG or CHG/IPA, with mean CHG concentration (and SEM) of 0.0190 (±0.0015) μg/mg tissue, 0.0021 (±0.0004) μg/mg tissue and 0.0022 μg/mg (±0.0018) tissue for CHG/EO, CHG and CHG/IPA respectively. At the top layers (0-300 μm) the mean CHG concentrations were 4.8 to 6.4-fold higher with CHG/EO compared to CHG alone and 2.7 to 20-fold higher with CHG/EO compared to CHG/IPA.

CHG Skin Penetration Following 24 h Exposure

The concentration of CHG extracted from all layers of the skin (0-1500 μm) was significantly higher in the presence of 50% (v/v) EO compared to CHG alone after 24 h permeation (p<0.05); the top 100 μm layer had a >2-fold increase (7.880 μg to 16.841 μg per mg tissue for CHG and CHG/EO treatments respectively) in the CHG concentration and the difference increased >5-fold within the deeper layers of the skin at 300 to 1500 μm depths [0.581 (±0.0466)μg to 3.123 (±0.16470) μg per mg tissue for CHG and CHG/EO respectively]. Data from this retention study were achieved by pooling together the data from five consecutive 20 μm and 30 μm skin sections (i.e. 100 μm sections from top to 600 μm depth and 150 μm sections from 600 to 1500 μm depth).

CHG Skin Penetration Following 24 h Exposure to IPA and Various Concentrations of EO The optimum concentration of EO which enhances CHG penetration into the skin was evaluated. Five percent (v/v) EO enabled significantly greater CHG skin penetration at the deeper layers of the skin (below 300 μm p<0.05) and 10% (v/v) EO significantly enhanced CHG skin penetration (p<0.05) within the top 900 μm compared to CHG alone. There were no significant differences (p>0.05) in the skin penetration of CHG from aqueous 2% (w/v) CHG and 2% (w/v) CHG with 70% (v/v) IPA.

Figure 2:
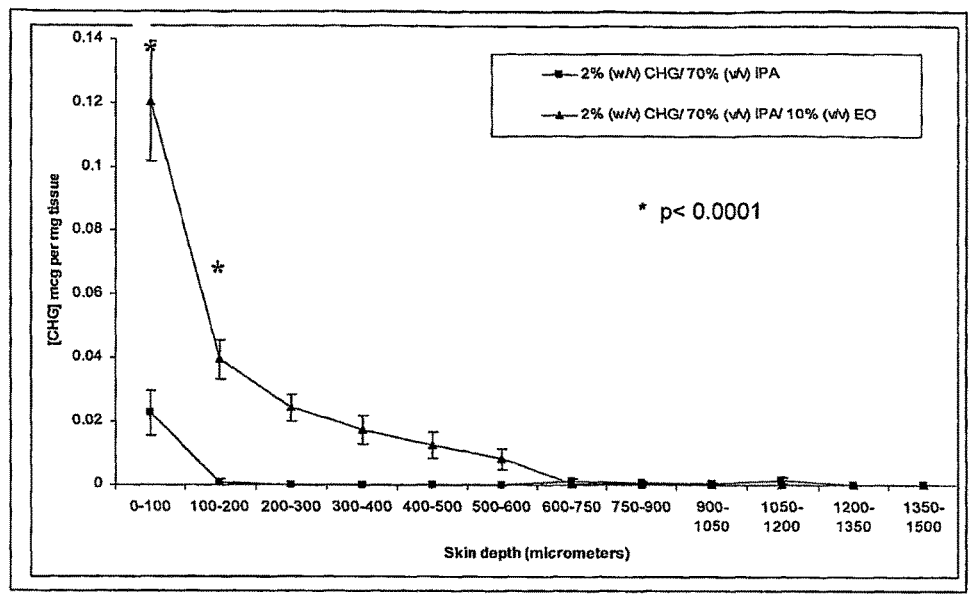
FIG. 2 illustrates the concentration of CHG (μg) extracted per mg of skin at various depths of full thickness human skin, after exposure to 2% (w/v) CHG when combined with 70% (v/v) IPA, with or without 10% (v/v) eucalyptus oil, for two minutes (Panel A) and thirty minutes (Panel B), n=15 for all conditions except 2% CHG/70% IPA/10% eucalyptus oil 2 minute exposure, where n=10.
Figure 2:
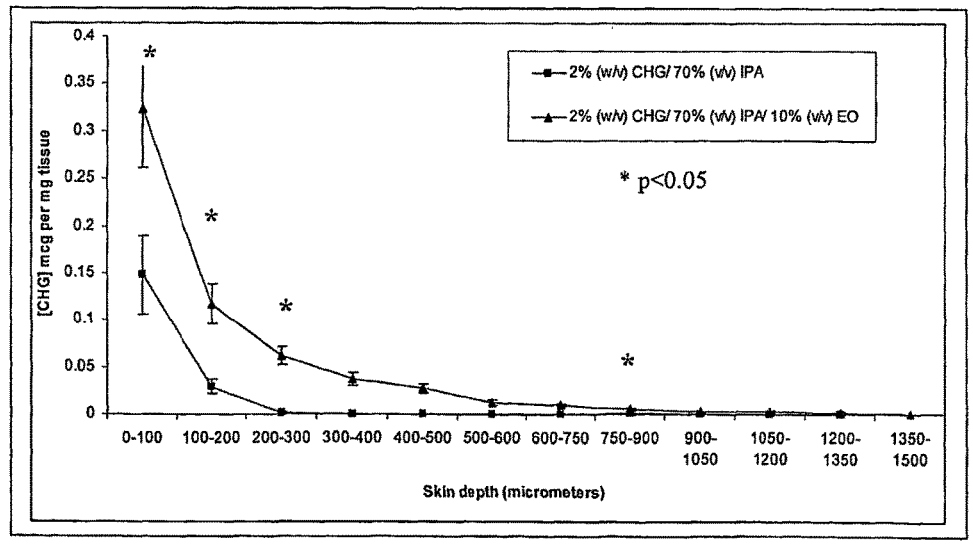

The optimum EO concentration, which enhanced CHG penetration into the full thickness human skin, was further evaluated in combination with 2% (w/v) CHG in 70% (v/v) IPA. Ten percent (v/v) EO in combination with 2% (w/v) CHG in 70% (v/v) IPA demonstrated enhanced CHG skin penetration after 2 min and 30 min exposure compared to 2% (w/v) CHG/70% (v/v) IPA alone (p<0.05; FIG. 2).

REFERENCES

The following references which are referred to above are all incorporated herein by reference.

Adams, D. H., An evaluation of three strategies to reduce device related infection associated with hypodermic needles and peripheral vascular catheters, 2006, PhD thesis, Aston University.

Al-Shuneigat, J., Cox, S. D., Markham, J. L., Effects of a topical essential oil containing formulation on biofilm-forming coagulase-negative *staphylococci*, *Letters in Applied Microbiology*, 2005, 41, 52-55.

Biruss, B., Kählig, H., Valenta, C., Evaluation of an eucalyptus oil containing topical drug delivery system for selected steriod hormones, *International Journal of Pharmaceutics*, 2007, 328, 142-151.

Block, C., Furman, M., Association between intensity of chlorhexidine use and micro-organisms of reduced susceptibility in a hospital environment, *Journal of Hospital Infection*, 2002, 51, 201-206.

Caelli, M., Porteous, J., Carson, C. F., Heller, R., Riley, T. V., Tea tree oil as an alternative topical decolonization agent for methicillin-resistant *Staphylococcus aureus*, *Journal of Hospital Infection*, 2000, 46, 236-237.

Constant, H., Falson, F., Pirot, F., Current and new strategies for the delivery of antiseptic agents, *Current Drug delivery*, 2006, 3(3), 315-323.

Cowan, M. M., Plant Products as Antimicrobial Agents, *Clinical Microbiology Reviews*, 1999, 12, 564-582.

Dryden, M. S., Dailly, S., Crouch, M., A randomized, controlled trial of tea tree topical preparations versus a standard topical regimen for the clearance of MRSA colonization, *Journal of Hospital Infection*, 2004, 56, 283-286.

Dursun, N., Liman, N., Ozyazgan I., Gunes, I., Saraymen, R., Role of thymus oil in burn healing, *Journal of Burn Care Rehabilitation*, 2003, 24 (6), 395-399.

Elliott, T. S., Moss, H. A., Tebbs, S. E., Wilson, I. C., Bonser, R. S., Graham, T. R., Burke, L. P., Faroqui, M. H., Novel approach to investigate a source of microbial contamination of central venous catheters, *European Journal of Clinical Microbiology*, 1997, 16, 210-213.

Fang, J., Leu, Y. L., Hwang, T. L., Cheng, H. C., Essential oils form sweet basil (*Ocimum basilicum*) as novel enhancers to accelerate transdermal drug delivery, *Biological and Pharmaceutical Bulletin*, 2004, 27, 1819-1825.

Filoche, S. K., Soma, K., Sissons, C. H., Antimicrobial effects of essential oils in combination with chlorhexidine digluconate, *Oral Microbiology and Immunology*, 2005, 20, 221-225.

Fraise, A. P., Susceptibility of anticiotic-resistant cocci to biocides, *Journal of Applied Microbiology*, 2002, 92, Suppl 158S-162S (Review).

Freeman, D. J., Falkiner, F. R., Keane, C. T,. New method for detecting slime production by coagulase negative *staphylococci*, *Journal of Clinical Pathology*, 1989, 42 (8), 872-874.

Gristina, A. G., Jennings, R. A., Naylor, P. T., Myrvik, Q. N., Webb, L. X., Comparative In Vitro Antibiotic Resistance of Surface-Colonizing Coagulase-Negative *Staphylococci*, *Antimicrobial Agents and Chemotherapy*, 1989, 33, 813-816.

Handbook of Pharmaceutical Excipients, $2^{nd}$ edition, 1994.

Karpanen, T. J., Worthington, T., Conway, B., Lambert, P. A., 2006 (POSTER).

Köljalq, S., Naaber, P. and Mikelsaarm M., Antibiotic resistance as an indicator of bacterial chlorhexidine susceptibility, *Journal of Hospital Infection,* 2002, 51, 106-113.

Lafforgue, C., Carret, L., Falson, F., Reverdy, M. E., Freney, J., Percutaneous absorption of a chlorhexidine digluconate solution, *International Journal of Pharmaceutics,* 1997, 147, 243-246.

Langgartner, K., Linde, H. J., Lehn, N., Reng, M., Schölmerich, J., Glück, T.,
Combined skin disinfection with chlorhexidine/propanol and aqueous povidone-iodine reduces bacteria colonisation of central venous catheters. *Intensive Care Medicine,* 2004, 30, 1081-1088.

McDonnell, G., Russell, A. D., Antiseptics and Disinfectants: Activity, Action and Resistance, *Clinical Microbiology Reviews,* 1999, 12, 147-179.

Messager, S., Hammer, K. A., Carson, S. F., Riley, T. V., Effectiveness of hand-cleansing formulations containing tea tree oil assessed ex vivo on human skin and in in vivo with volunteers using European Standard EN1499, *Journal of Hospital Infection,* 2005, 59, 220-228.

NCCLS (National Committee for Clinical Laboratory Standards), Performance standards for antimicrobial disk susceptibility test, (6$^{th}$ edition), Approved Standard, M2-A6, Wayne Pa., 1997.

Pfaller, M. A., Jones, R. N., Doern, G. V., Sader, H. D., Kugler, K. C., Beach, M. L., Survey of blood stream infections attributed to gram-positive cocci: frequency of occurrence and antimicrobial susceptibility of isolates collected in 1997 in the United States, Canada, and Latin America from the SENTRY Antimicrobial Surveillance Program, SENTRY Participants Group, *Diagn Microbiol Infect Dis,* 1999, 33, 283-297.

Reichling, J., Landvatter, U., Wagner, H., Kostka, K-H, Schaefer, U.F., In vitro studies on release and human skin permeation of Australian tee tree oil (TTO) from topical formulations, *European Journal of Pharmaceuticals and Biopharmaceutics,* 2006, 64, 222-228.

Remington's Pharmaceutical Sciences, 18$^{th}$ edition, Mack Publishing Company, Easton, Pa., 1990.

Richards, M. J., Edwards, J. R., Culver, D. H., Gaynes, R. P., Nosocomial infections in combined medical-surgical intensive care units in the United States, *Infect Control Hosp Epidemiol.,* 2000, 21, 510-515.

Rupp, M. E., Archer, G. L., Coagulase-negative *staphylococci:* pathogens associated with medical progress, *Clinical Infectious Diseases,* 1994, 19, 231-243.

Sadovskaya, I., Vinogradov, E., Flahaut, S., Kogan, G., Jabbouri, S., Extracellular carbohydrate-containing polymers of a model biofilm-producing strain, *Staphylococcus epidermidis* RP62A, *Infection and Immunity,* 2005, 73 (5), 3007-317.

Saginur, R., St. Denis, M., Ferris, M., Aaron, S. D., Chan, F., Lee, C., Ramotar, K., Multiple Combination Bactericidal Testing of *Staphylococcal* Biofilms from Implant-Associated Infections, *Antimicrobial Agents and Chemotherapy,* 2006, 50, 55-61.

Shin, S., Lim, S., Antifungal effects of herbal essential oils alone and in combination with ketoconazole against *Trichophyton* spp, *Journal of Applied Microbiology,* 2004, 97, 1289-1296.

Traoré, O., Allaert, F. A., Fournet-Fayard, S., Verrière, J. L., Laveran, H., Comparison of in-vivo antibacterial activity of two skin disinfection procedures for insertion of peripheral vascular catheters: povidone iodine versus chlorhexidine, *Journal of Hospital Infection,* 2000, 44, 147-150.

Walsh, S. E., Maillard, J. Y., Russell, A. D., Catrenich, C. E., Charbonneau, D. L., Bartolo, R. G., Development of bacterial resistance to several biocides and effects on antibiotic susceptibility, *Journal of Hospital Infection,* 2003, 55, 98-107.

Warnke, P. H., Sherry, E., Russo, P. A. J., Acil, Y., Willtfang, J., Sivananthan, S., Sprengel, M., Roldan, J. C., Schubert, S., Bredee, J. P., Springer, I. N. G., Antibacterial essential oils in malodorous cancer patients: Clinical observations in 30 patients, *Phytomedicine,* 2006, 13, 463-467.

Williams, A. C., Barry, B. W., Penetration Enhancers, *Advanced Drug Delivery Reviews,* 56, 603-618

The invention claimed is:

1. A method for the prevention of infection in intact skin, below the stratum corneum, prior to an invasive medical procedure, comprising contacting the intact skin prior to the invasive medical procedure with a composition comprising: 0.1% to 5% chlorhexidine by weight (w/v), 50% to 90% isopropyl alcohol (v/v), and 5% to 10% eucalyptus oil (v/v).

2. The method according to claim 1, wherein the chlorhexidine is chlorhexidine digluconate.

3. The method according to claim 1, wherein the infection to be prevented is from *S. epidermidis.*

4. The method according to claim 1, wherein the infection to be prevented is at a depth of up to 3000 μm in the skin layer.

5. The method according to claim 3, wherein the infection to be prevented is at a depth of up to 1000 μm in the skin layer.

6. The method according to claim 1, wherein the infection to be prevented is at a depth of greater than 100 μm in the skin layer.

7. The method according to claim 6, wherein the infection to be prevented is at a depth of beyond 480 μm in the skin layer.

8. The method according to claim 1, wherein the infection to be prevented is at a depth of between 100 and 3000 μm in the skin layer.

9. The method according to claim 8, wherein the infection to be prevented is at a depth of between 480 and 1000 μm in the skin layer.

10. The method according to claim 1, wherein the infection to be prevented is in the dermis.

11. The method according to claim 1, wherein the infection to be prevented is in the hair follicle.

12. The method according to claim 1, wherein the only antimicrobial ingredients in the composition are chlorhexidine, eucalyptus oil and isopropyl alcohol.

13. The method according to claim 1, wherein the composition comprises: 2% chlorhexidine by weight (w/v), 70% isopropyl alcohol (v/v), and 5% to 10% eucalyptus oil (v/v).

14. The method according to claim 1, wherein the composition comprises: 2% chlorhexidine by weight (w/v), 70% isopropyl alcohol (v/v), and 5% eucalyptus oil (v/v).

15. The method according to claim 1, wherein the composition comprises: 2% chlorhexidine by weight (w/v), 70% isopropyl alcohol (v/v), and 10% eucalyptus oil (v/v).

16. A method for the prevention of infection from *S. epidermidis* in intact skin, below the stratum corneum, prior to an invasive medical procedure, comprising contacting the *S. epidermidis* in intact skin prior to the invasive medical procedure with a composition comprising: 0.1% to 5% chlorhexidine by weight (w/v), 50% to 90% isopropyl alcohol (v/v), and 5% to 10% eucalyptus oil (v/v).

17. The method according to claim 16, wherein the infection is a skin infection.

18. The method according to claim 16, wherein the chlorhexidine is chlorhexidine digluconate.

19. The method according to claim 16, wherein the only antimicrobial ingredients in the composition are chlorhexidine, eucalyptus oil and isopropyl alcohol.

20. The method according to claim 16, wherein the composition comprises: 2% chlorhexidine by weight (w/v), 70% isopropyl alcohol (v/v), and 5% to 10% eucalyptus oil (v/v).

21. The method according to claim 16, wherein the composition comprises: 2% chlorhexidine by weight (w/v), 70% isopropyl alcohol (v/v), and 5% eucalyptus oil (v/v).

22. The method according to claim 16, wherein the composition comprises: 2% chlorhexidine by weight (w/v), 70% isopropyl alcohol (v/v), and 10% eucalyptus oil (v/v).

23. A method for the prevention of infection in intact skin, below the stratum corneum, prior to an invasive medical procedure, comprising:
   contacting an area of intact skin, prior to the invasive medical procedure, with a composition comprising: 0.1% to 5% chlorhexidine by weight (w/v), 50% to 90% isopropyl alcohol (v/v), and 5% to 10% eucalyptus oil (v/v); and
   performing the invasive medical procedure at the contacted area of intact skin.

24. The method according to claim 23, wherein the invasive medical procedure comprises introducing a surgical apparatus below the contacted area of intact skin during surgery.

25. The method according to claim 23, wherein the invasive medical procedure comprises insertion of a catheter at the contacted area of intact skin.

26. The method according to claim 23, wherein the infection is from *S. epidermidis*.

27. The method according to claim 23, wherein the only antimicrobial ingredients in the composition are chlorhexidine, eucalyptus oil and isopropyl alcohol.

28. The method according to claim 23, wherein the composition comprises: 2% chlorhexidine by weight (w/v), 70% isopropyl alcohol (v/v), and 5% to 10% eucalyptus oil (v/v).

29. The method according to claim 23, wherein the composition comprises: 2% chlorhexidine by weight (w/v), 70% isopropyl alcohol (v/v), and 5% eucalyptus oil (v/v).

30. The method according to claim 23, wherein the composition comprises: 2% chlorhexidine by weight (w/v), 70% isopropyl alcohol (v/v), and 10% eucalyptus oil (v/v).

* * * * *